(12) United States Patent
Adams et al.

(10) Patent No.: US 9,125,985 B2
(45) Date of Patent: Sep. 8, 2015

(54) NEEDLE WITH PROTECTIVE COVER MEMBER

(71) Applicants: Kyle S. Adams, Dallas, TX (US); Gordon E. Atkinson, Hickory, NC (US)

(72) Inventors: Kyle S. Adams, Dallas, TX (US); Gordon E. Atkinson, Hickory, NC (US)

(73) Assignee: iMed Technology, Inc., Dallas, TX (US)

( * ) Notice: Subject to any disclaimer, the term of this patent is extended or adjusted under 35 U.S.C. 154(b) by 346 days.

(21) Appl. No.: 13/854,308

(22) Filed: Apr. 1, 2013

(65) Prior Publication Data

US 2014/0296795 A1 Oct. 2, 2014

(51) Int. Cl.
*A61M 5/162* (2006.01)
*A61M 5/50* (2006.01)
*A61M 5/158* (2006.01)

(52) U.S. Cl.
CPC .............. *A61M 5/1626* (2013.01); *A61M 5/158* (2013.01); *A61M 5/50* (2013.01)

(58) Field of Classification Search
CPC ..... A61M 5/142; A61M 5/1626; A61M 5/50; A61M 5/322
See application file for complete search history.

(56) References Cited

U.S. PATENT DOCUMENTS

| | | | |
|---|---|---|---|
| 4,564,054 A | 1/1986 | Gustavsson | |
| 5,336,187 A | 8/1994 | Terry et al. | |
| 5,336,199 A * | 8/1994 | Castillo et al. | 604/198 |
| 5,364,370 A * | 11/1994 | Szerlip et al. | 604/263 |
| 5,685,860 A | 11/1997 | Chang et al. | |
| 5,755,699 A | 5/1998 | Blecher et al. | |
| 6,165,157 A | 12/2000 | Dillon et al. | |
| 6,500,155 B2 | 12/2002 | Sasso | |
| 6,537,255 B1 | 3/2003 | Raines | |
| 6,623,458 B2 | 9/2003 | Woehr et al. | |
| 6,676,633 B2 | 1/2004 | Smith et al. | |
| 6,824,530 B2 | 11/2004 | Wagner et al. | |
| 7,083,600 B2 * | 8/2006 | Meloul | 604/263 |
| 7,147,624 B2 * | 12/2006 | Hirsiger et al. | 604/198 |
| 7,214,208 B2 | 5/2007 | Vaillancourt | |
| 7,347,842 B2 | 3/2008 | Thorne et al. | |
| 7,534,231 B2 | 5/2009 | Kuracina et al. | |
| 7,611,487 B2 | 11/2009 | Woehr et al. | |
| 7,717,888 B2 | 5/2010 | Vaillancourt et al. | |
| 7,758,544 B2 | 7/2010 | Solomon et al. | |
| 7,776,016 B1 | 8/2010 | Halseth et al. | |
| 7,927,314 B2 | 4/2011 | Kuracina et al. | |
| 8,066,678 B2 | 11/2011 | Vaillancourt et al. | |
| 2004/0199112 A1 * | 10/2004 | Dalton | 604/110 |
| 2008/0119795 A1 | 5/2008 | Erskine | |
| 2012/0004619 A1 | 1/2012 | Stephens et al. | |
| 2012/0046621 A1 | 2/2012 | Vaillancourt et al. | |

* cited by examiner

*Primary Examiner* — Quynh-Nhu H Vu
(74) *Attorney, Agent, or Firm* — Stevens & Showalter LLP

(57) ABSTRACT

A safety needle assembly including a medical needle and a needle protection assembly. The needle protection assembly includes a cover member surrounding a portion of the medical needle and is movable between a retracted position and an extended position. A base sub-assembly of the needle protection assembly is attached to an end of the cover member and includes a base plate defining a through hole receiving the medical needle therethrough in the retracted condition of the needle protection assembly. A needle stop member, including an integrally formed spring portion and stop plate, is positioned on a planar side of the base plate, and the spring portion biases the stop plate in linear movement to cover the hole in response to movement of the needle protection assembly to the extended condition.

19 Claims, 6 Drawing Sheets

ND PROTECTIVE COVER
NEEDLE WITH PROTECTIVE COVER MEMBER

FIELD OF THE INVENTION

The present invention relates to medical hypodermic needles and Huber safety needles and, more particularly, to a medical needle provided with a protective device to reduce the risk of an inadvertent needle stick.

BACKGROUND OF THE INVENTION

Medical devices for injecting or infusing liquid medications, and including devices for withdrawing patient body fluids typically use a hypodermic needle that is inserted into the patient's body. For example, an infusion device commonly used is a Huber needle that is adapted for insertion in a permanent medical site on a patient to administer liquid medications.

A common concern associated with use of medical needles is avoidance of inadvertent needle stick injuries following removal of a needle from the patient in order to prevent, for example, transfer of microbial contaminants and infectious diseases. Various safety features have been proposed to prevent contact with the needle following a clinical procedure, such as providing a separate sheath member that may be placed over the needle and providing a collapsible or movable sheath structure that can extend to cover and remain over the needle at the end of a procedure. Exemplary safety devices for use on medical needles are disclosed in U.S. Pat. Nos. 5,336,199 and 7,083,600.

SUMMARY OF THE INVENTION

In accordance with an aspect of the present invention, a combination including a medical needle and a needle protective device is provided. The combination comprises a needle support supporting a medical needle having an exposed tip, and a needle protection assembly. The needle protection assembly includes a cover member having a first end attached to the needle support in surrounding relation to a portion of the medical needle, and the needle protection assembly has a retracted condition and an extended condition. The needle protection assembly additionally includes a base sub-assembly attached to a second end of the cover member. The base sub-assembly comprises: a) a base member including a planar base plate defining a through hole receiving the medical needle therethrough in the retracted condition of the needle protection assembly; and b) a needle stop member comprising an integrally formed spring portion and stop plate. Both the spring portion and the stop plate lie on a planar side of the base plate, and the spring portion biases the stop plate in linear movement to cover the hole in response to movement of the needle protection assembly to the extended condition.

The cover member may comprise a spiral coil, and the spiral coil may include a reduced coil diameter at the first end of the cover member attached to the needle support and an enlarged coil diameter at the second end of the cover member attached to the base member. The spiral coil may be formed of an elongated planar member formed as a rolled planar ribbon having a width and a length, wherein the width of the planar ribbon extends generally parallel to the medical needle.

The integrally formed spring portion and stop plate may be molded of a resin material.

The spring portion may include opposing arcuate sides extending from the stop plate, and the arcuate sides may each have a concave edge and the concave edges may face inwardly toward each other.

The needle stop member may be movable between first and second positions, the arcuate sides being flexed outwardly from each other in the first position and biasing the stop plate in engagement against the medical needle, and the arcuate sides moving toward each other during the linear movement of the stop plate in response to movement of the needle protection assembly to the extended condition.

The spring portion may define a continuous inner circumference connecting the opposing arcuate sides.

The base plate may include first and second axially spaced planar portions generally perpendicular to the medical needle, and the second planar portion may define a recessed area in the base plate containing the needle stop member.

A stop retainer plate may be supported on the first planar portion of the base plate and may extend over the needle stop member to retain the needle stop member between the stop retainer plate and the second planar portion.

In accordance with another aspect of the invention, a combination including a medical needle and a needle protective device is provided. The combination comprises a needle support supporting a medical needle having an exposed tip and a needle protection assembly. The needle protection assembly includes a cover member having a first end attached to the needle support in surrounding relation to a portion of the medical needle, and the needle protection assembly has a retracted condition and an extended condition. The needle protection assembly additionally includes a base sub-assembly attached to a second end of the cover member. The base sub-assembly comprises: a) a base member including a planar base plate, and an enclosure wall extending from the base plate and defining a hollow enclosure receiving the second end of the cover member, and the base plate defines a through hole receiving the medical needle therethrough in the retracted condition of the needle protection assembly; and b) a needle stop member comprising a spring portion and stop plate. The spring portion is configured as an elastically resilient ring shaped member including opposing arcuate sides extending from a proximal location attached on the stop plate to a distal location adjacent to the enclosure wall. Both the spring portion and the stop plate lie on a planar side of the base plate, and the spring portion biases the stop plate in linear movement to cover the hole in response to movement of the needle protection assembly to the extended condition.

The enclosure wall may define a diameter on the base plate, and a distance between the stop plate and the distal location on the spring portion is equal to about one-half the diameter.

The base plate may include first and second axially spaced planar portions generally perpendicular to the medical needle, and the second planar portion may define a recessed area in the base plate containing the needle stop member. An axial wall may extend between the first and second planar portions and may define an abutment for engaging the stop plate during the linear movement of the stop plate in response to movement of the needle protection assembly to the extended condition.

The spring portion and the stop plate may be formed as an integrally molded component.

The needle support may include a circular flange extending perpendicular to the needle, and the flange may be sized to rest against the enclosure wall and cover the spiral coil in the retracted condition of the needle protection assembly.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
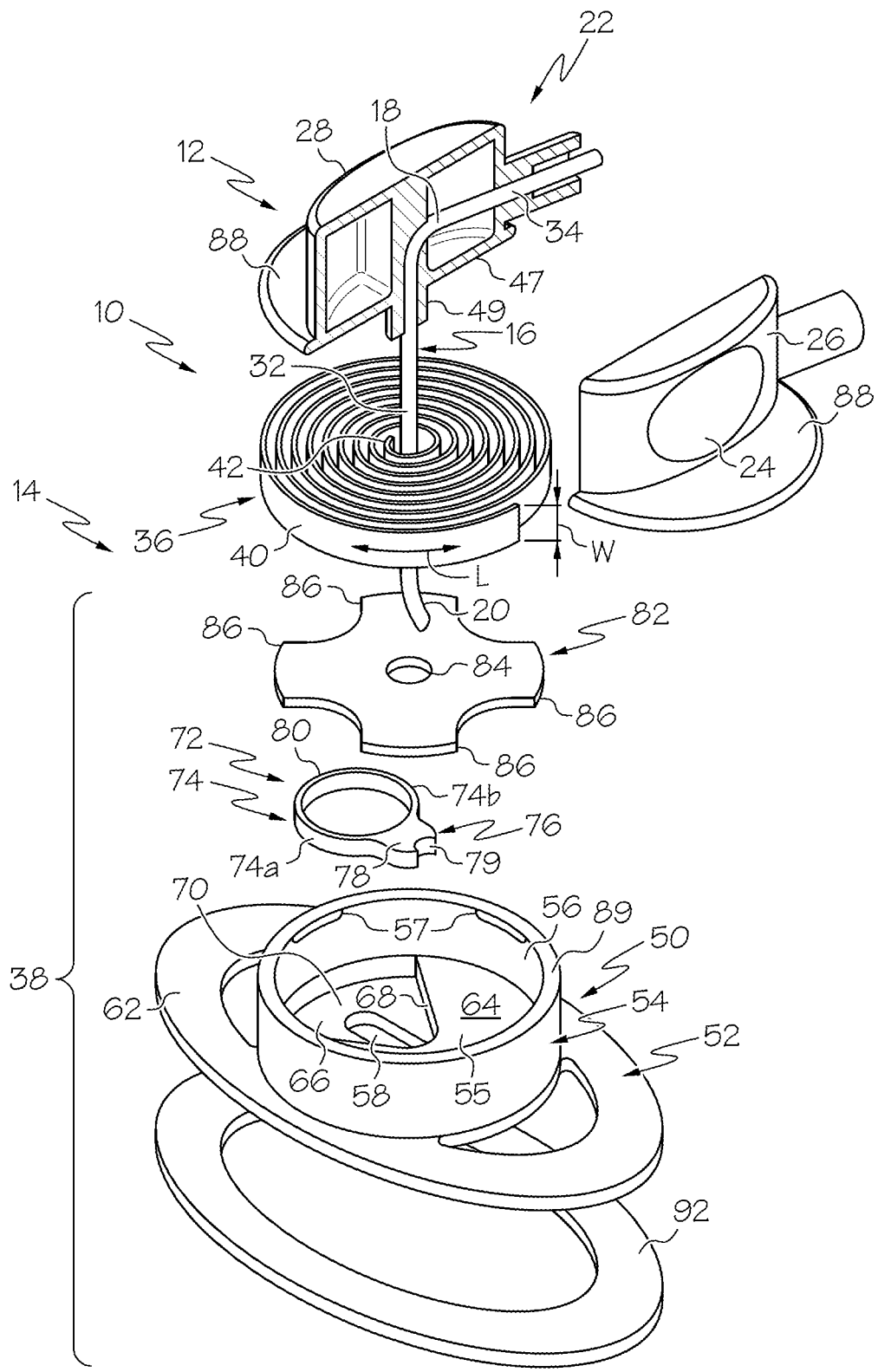
FIG. 1 is an exploded perspective view of a safety needle assembly in accordance with an aspect of the invention.

Referring to FIG. 1, the present invention provides a safety needle assembly 10 including, in combination, a needle assembly 12 and a needle protection assembly 14. The needle assembly 12 includes a medical needle 16, depicted as a Huber needle, having a proximal end 18 and a sharpened distal end 20, and a needle hub 22 defining a needle support that at least partially surrounds the proximal end 18 of the needle 16. The needle hub 22 is generally shaped as an elliptical cylinder to conform to a user's hand, and may additionally include shallow indentations 24 on opposing sides 26, 28 for accommodating a user's fingers.

The medical needle 16 is illustrated as a conventional Huber needle and includes a bend at the proximal end 18. A first portion 32 of the needle 16 extends from the hub 22 at a central location of the hub 22, and a second portion 34 of the needle 16 extends perpendicular to the first portion 32 and parallel to a major axis of the hub 22. The hub 22 is preferably formed of a resin material, and is illustrated herein as a two piece assembly for rigidly retaining the needle 16 between the two halves of the assembly. In addition to the assembly shown, it should be understood that the resin material of the hub may be formed around the needle 16 by a molding operation, e.g., by insert molding.

The needle protection assembly 14 includes a cover member 36 attached to the hub 22, and a base sub-assembly 38 attached to the cover member 36. The cover member 36 is formed as a spiral coil member and is preferably an elongated planar member having a configuration corresponding to a constant force spring. In particular, the cover member 36 is a coil formed by a continuous rolled planar ribbon 40 having a width dimension, W, and a length dimension, generally depicted by L and extending from one longitudinal end of the ribbon 40 to the opposing longitudinal end of the ribbon 40. An inner end 42 of the ribbon 40 defines a minimum or reduced coil diameter, which also defines a first end 44 (FIG. 4B) of the cover member 36 attached to the hub 22. For example, a lower side 47 the hub 22 may include an integrally formed downwardly extending cylindrical support 49 through which the needle 16 passes, and the first end 44 of the cover member 36 is affixed, such as by bonding or mechanical attachment, to an outwardly facing surface of the cylindrical support 49.

An outer end 46 of the ribbon 40 defines a maximum or enlarged coil diameter, which also defines a second end 48 (FIG. 4B) of the cover member 36 attached to a base member 50 of the base sub-assembly 38. The ribbon 40 preferably comprises a resin material molded in a rolled or coiled configuration, such that its "normal" or unstressed condition is as seen in FIGS. 1 and 4A.

Referring to FIG. 1, the base member 50 of the base sub-assembly 38 preferably comprises a molded resin member and includes a planar base plate 52, and a circular enclosure wall 54 that is affixed to and extends perpendicular from an upper side 62 of the base plate 52. The base plate 52 and enclosure wall 54 may be molded as an integral structure. The enclosure wall 54 includes an inner surface 56 forming a hollow enclosure 55 and defining a diameter that is generally equal to the maximum or enlarged coil diameter of the second end 48 of the cover member 36, and the second end 48 of the cover member 36 is received in engagement within the enclosure wall 54 where it is affixed to the inner surface 56, such as by bonding or mechanical attachment. For example, a mechanical attachment structure such as inwardly extending tabs 57 may be provided at an outer edge of the enclosure wall 54 for retaining the second end 48 of the cover member 36 in the enclosure 55.

Figure 3A:
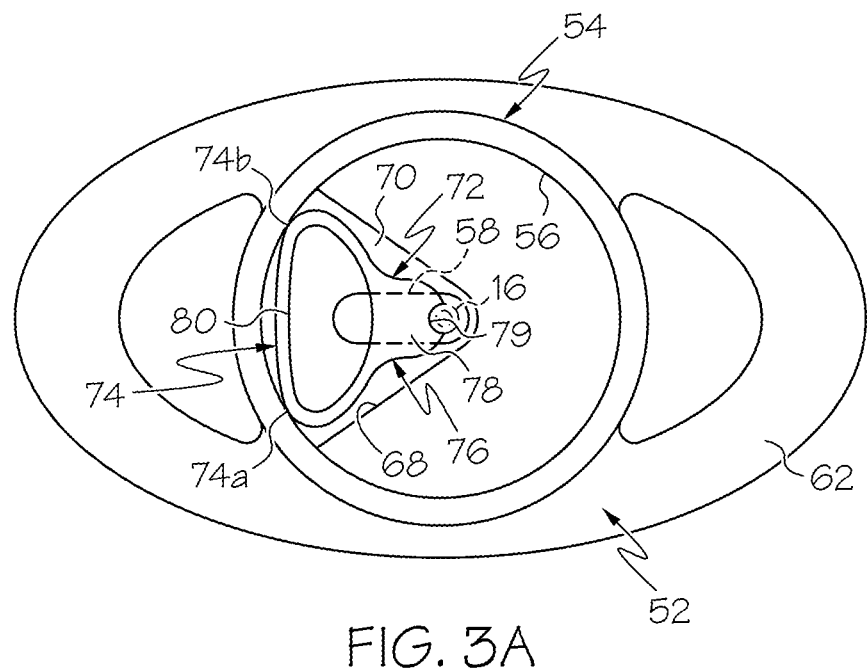
FIG. 3A is a plan view of a base sub-assembly for the safety needle assembly with a needle stop retainer plate removed and showing a needle stop member in a first position.
Figure 3B:
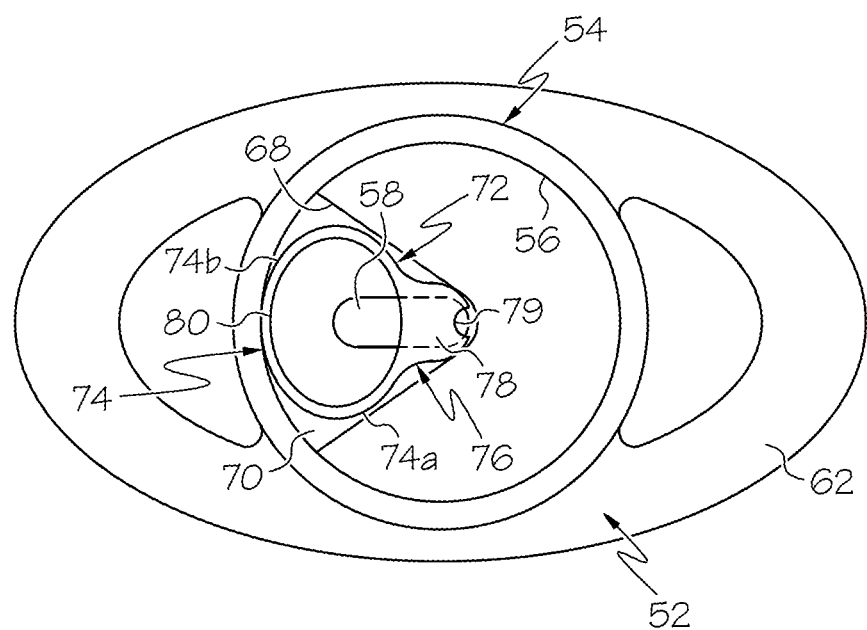
FIG. 3B is a plan view similar to FIG. 3A showing the needle stop member in a second position.
Figure 4A:
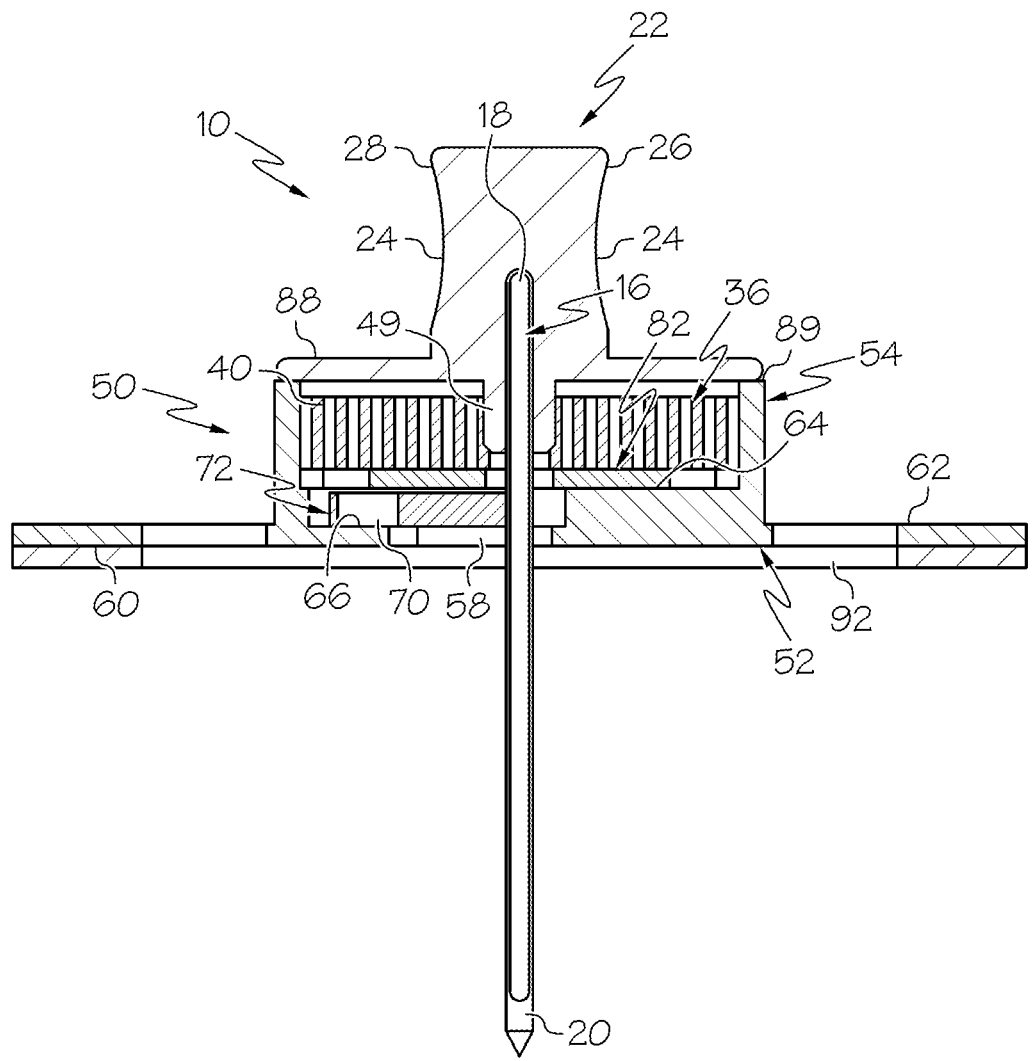
FIG. 4A is a cross-sectional view taken along line 4A-4A in FIG. 2A.

Referring to FIGS. 1, 3A and 3B, the base plate 52 includes a hole 58, illustrated as an elongated slot, for receiving the needle 16 (FIG. 4A). As will be discussed further below, the needle 16 is oriented perpendicular to the base plate 52 and is movable through the hole 58 from a position extending from a lower side 60 of the base plate 52 (FIG. 4A), to a position retracted from the hole 58 and located above the upper side 62 of the base plate 52 (FIG. 4B).

Figure 4B:
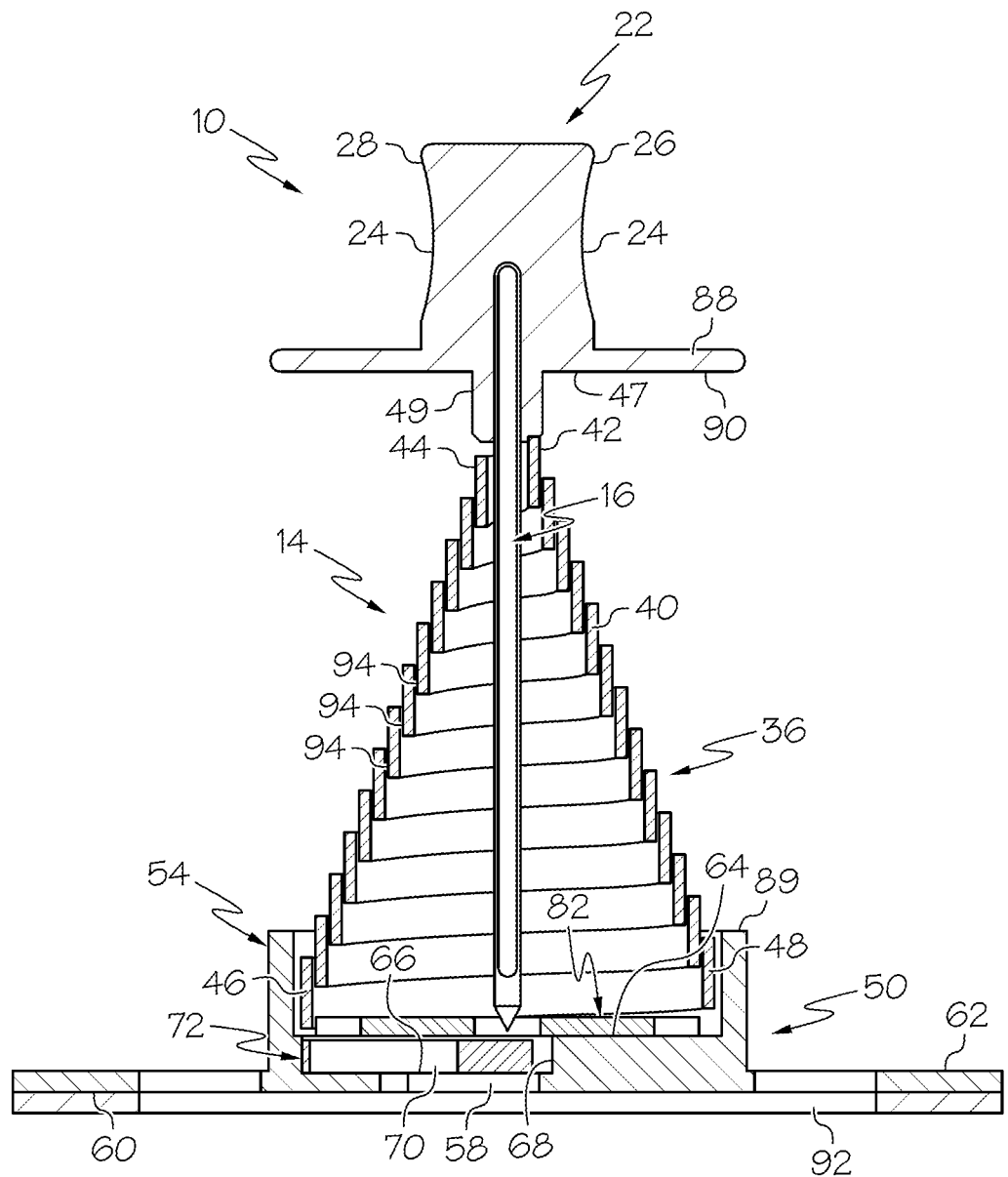
FIG. 4B is a cross-sectional view taken along line 4B-4B in FIG. 2B.

Referring to FIGS. 1, 4A and 4B, the base plate 52 additionally includes a first planar portion 64 and a second planar portion 66 extending generally perpendicular to the needle 16. The first and second planar portions 64, 66 both face axially toward the lower side 47 of the needle hub 22. The first planar portion 64 is spaced from the second planar portion 66 an axial distance extending in a direction parallel to the needle 16. An axial wall 68 extends between the first and second planar portions 64, 66 forming a V-shaped wall and defining a recess 70 having a bottom surface formed by the second planar portion 66.

Referring to FIG. 1, the base sub-assembly 38 further includes a needle stop member 72 which is configured to be positioned within the recess 70. The needle stop member 72 includes a spring portion 74 and a stop plate 76. The spring portion 74 and stop plate 76 are preferably formed as an integral structure from a resin material, and formation of the needle stop member 72 may be performed in a molding operation. The spring portion 74 is configured as an elastically resilient ring-shaped member including opposing arcuate sides 74a, 74b defining concave edges facing inwardly toward each other and defining continuous inner circumference connecting the arcuate sides 74a, 74b.

Referring additionally to FIGS. 3A and 3B, the arcuate sides 74a, 74b of the needle stop member 72 are attached to the stop plate 76 at a proximal location, generally identified at 78, and extend to a distal location 80 that is adapted to be located adjacent to the enclosure wall 54. The distance from an end of the stop plate 76 to the distal location 80 is about one-half the diameter of the enclosure 55 defined by the enclosure wall 54. Both the spring portion 74 and the stop plate 76 lie on the planar second portion 66 of the base plate 52 and define a flat construction, providing a compact configuration when the needle protection assembly 14 is in the retracted condition. A stop retainer plate 82 (FIGS. 4A and 4B) is supported on the first planar surface 64, and extends over the recess 70 to retain the needle stop member 72 between the stop retainer plate 82 and the second planar portion 66.

As seen in FIG. 1, the stop retainer plate 82 includes an aperture 84 for passage of the needle 16. Further, the stop retainer plate 82 includes four radially extending arms 86 having outer arcuate edges defining a radius of curvature matching the radius of curvature of the enclosure wall 54 for engaging the inner surface 56 to center the stop retainer plate 82 within the enclosure wall 54. It should be understood that the stop retainer plate 82 may be affixed in place on the first planar portion 64 by any means that prevents movement of the stop retainer plate relative to the base plate 52, such as by bonding to either the first planar portion 64 or the enclosure wall 54, or by a mechanical attachment to either the enclosure wall 54 or the first planar portion 64.

The needle stop member 72 is movable between a first position, as illustrated in FIGS. 3A and 4A, and a second position, as illustrated in FIGS. 3B and 4B. In the first position, the needle protection assembly 14 is located in a retracted condition, locating the needle 16 extending through the hole 58. In addition, the first position of the needle stop member 72 locates the stop plate 76 displaced from the hole 58 and engaged against the side of the needle 16, with the arcuate sides 74a, 74b of the ring portion 74 flexed outwardly from each other to create a biasing force that biases the stop plate 76 against the needle 16. It may be noted that an end of the stop plate 76 includes a groove area 79 for engaging around a portion of the needle 16 to maintain alignment of the end of the stop plate 76 on the needle 16. Further, the V-shape defined by the axial wall 68 is sized to accommodate the outward extension of the arcuate sides 74a, 74b when the needle stop member 72 is in the first position, while also limiting sideways displacement of the spring portion 74.

The needle protection assembly 14 is movable to an extended condition, positioning the needle 16 to a retracted location displacing the needle from the hole 58 and the stop plate 76, and in which the second end 20 of the needle 16 is positioned above the base plate 52. As relative movement between the needle protection assembly 14 and the needle 16 positions the needle 16 out of engagement with stop plate 76, the biasing force applied by the spring portion 74 biases the stop plate 76 in linear movement over the hole 58 and positions the distal end of the stop plate 76 to abut in engagement with a portion of the axial wall 68 that forms an apex to the V-shaped area adjacent to the hole 58. Linear movement, as used herein, refers to movement of the stop plate 76 along a straight line and preferably along a diametric line passing through the location of the needle 16 positioned through the hole 58. The linear movement of the stop plate 76 is accompanied by movement of the arcuate sides 74a, 76a toward each other to the final position shown in FIG. 3B to maintain the stop plate 76 in the illustrated position covering the hole 58 and thereby prevent the needle 16 from reentering the hole 58. As may be seen in FIGS. 3A and 3B, the position of the needle stop member 72 is maintained in both the first and second positions by the angled sides of the axial wall 68 defining the recess 70 for containing the needle stop member 72.

It may be noted that the elongated configuration of the slot 58 is provided to facilitate assembly of the needle stop member 72 within the recess 70. In particular, during assembly of the safety needle assembly 10, it is necessary to hold the stop plate 76 away from the portion of the hole 58 that receives the needle 16. The elongated slot 58 provides additional access for means, such as a fixture (not shown), to be inserted through the base plate 52 for engagement with the needle stop member 72 to retain the stop plate 76 in a displaced position away from the path of the needle 16 as it is inserted through the base plate 52.

Figure 2A:
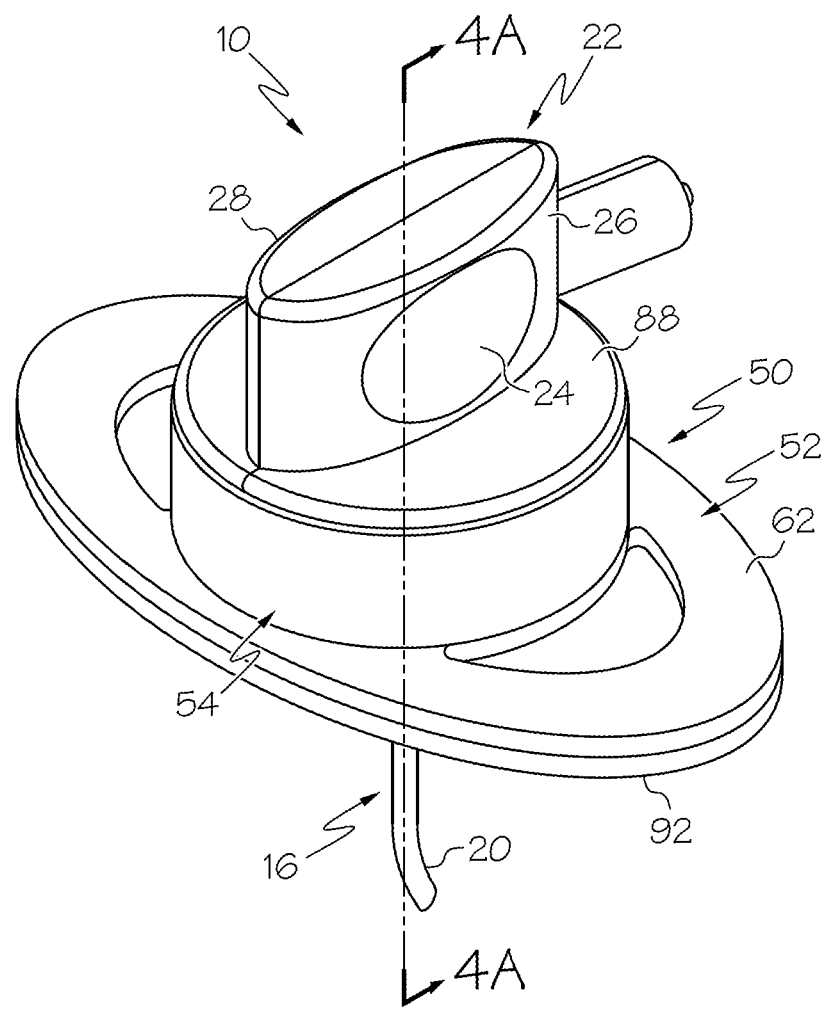
FIG. 2A is a perspective view of the safety needle assembly illustrated in a configuration with a needle protection assembly in a retracted condition.

In a procedure using the safety needle assembly 10, the needle protection assembly 14 is initially located in the collapsed condition illustrated in FIGS. 2A, 3A and 4A with the coils of the cover member 36 lying in a common plane and contained within the enclosure wall 54. This is the natural, unstressed condition of the cover member 36, such that the cover member 36 will tend to maintain this position or condition of the needle protection assembly 14 without requiring a mechanism for preventing movement of the needle protection assembly 14 to the extended condition. The needle hub 22 includes a circular flange 88 extending radially outwardly at the lower side 47, perpendicular to the cylindrical support 49. The flange 88 has a diameter that is the same as the diameter of the enclosure wall 54 and engages an axial outer edge 89 of the enclosure wall 54 when the needle protection assembly 14 is in the retracted condition, as may be best seen in FIG. 4A. The flange 88 provides a protective cover for preventing debris from entering within the enclosure wall 54 and between the coils of the cover member 36, and further provides an engagement surface 90 (FIG. 4B) for positively locating the hub 22 in the initial position relative the base sub-assembly 38.

The initial configuration for the safety needle assembly 10 provides a compact configuration for insertion of the needle 16 into a site on a patient, such as an infusion site (not shown) permanently implanted in a patient and having an elastomeric septum for receiving the needle 16. In particular, a user or medical personnel may grip the hub 22 of the assembly 10 at the indentations 24, and use the hub 22 to direct the second end 20 of the needle into the infusion site. The needle 16 may be inserted to position the base plate 52 at or adjacent to the patient. For this purpose, the base plate 52 may be provided with a foam cushion or pad 92 to provide a comfortable engagement surface for engagement with the patient.

It should be noted that in accordance with an aspect of the invention, the compact configuration of the safety needle assembly 10 is facilitated by the generally flat construction of the needle stop member 72 and the coiled configuration of the cover member 36 contained within the enclosure 55 of the base member 50.

Figure 2B:
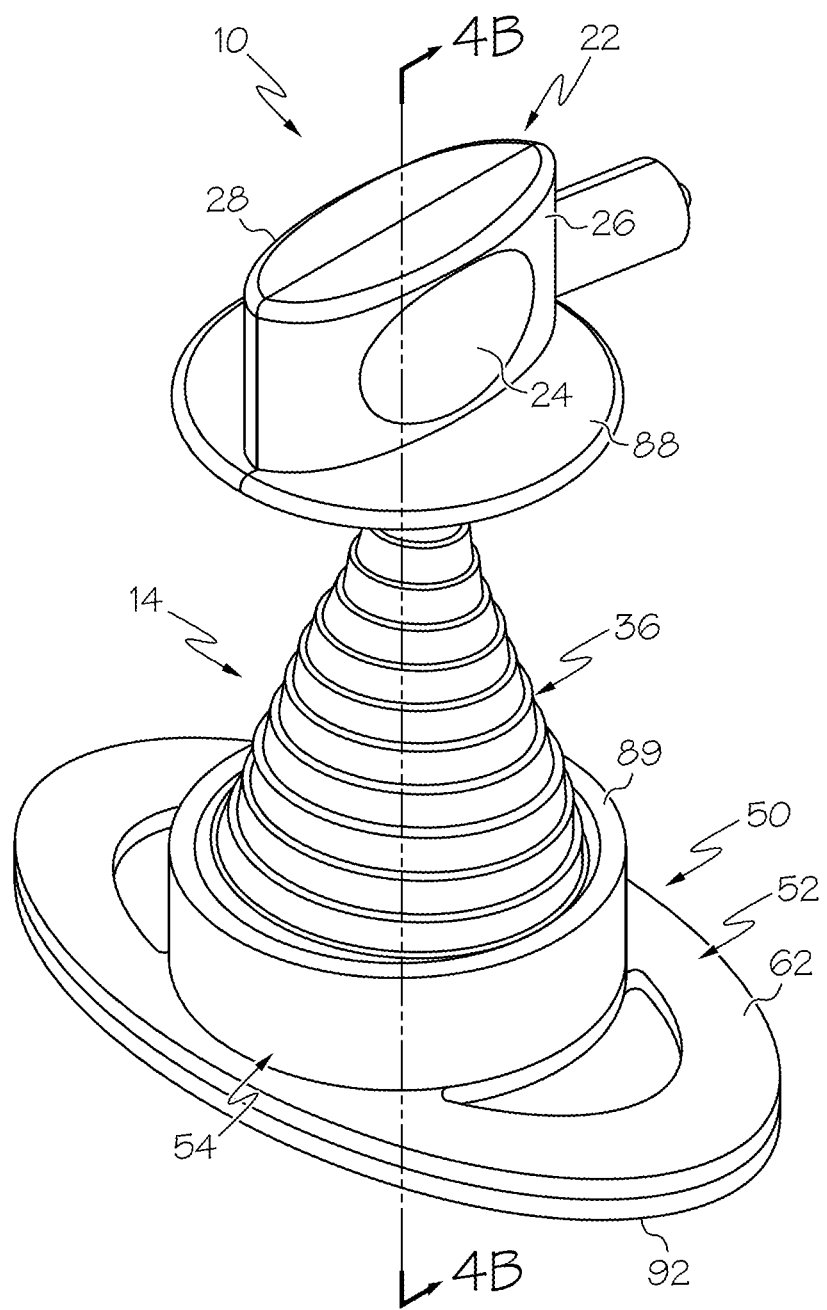
FIG. 2B is a perspective view of the safety needle assembly illustrated in a configuration with the needle protection assembly in an extended condition.

Subsequent to withdrawing the needle 16 from the site, it is desirable to protect personnel from a needle stick at the second end 20 of the needle 16. Accordingly, as the needle 16 is withdrawn from the site, or immediately after withdrawal of the needle 16, a relative movement between the base member 50 and the needle 16 is produced by the user or medical personnel providing a force to move the base member 50 and the hub 22 in opposite directions along the axis of the needle 16 to expand or extend the cover member 36. That is, as a result of the relative movement between the base member 50 and the hub 22, the coils of the cover member 36 are moved apart from each other in the direction parallel to the length of the needle 16, i.e., along the width-wise direction of the ribbon 40, to the position shown in FIGS. 2B and 4B. It may be understood that there is a slight spacing between the coils of the cover member, avoiding frictional binding and permitting passage of air through the cover member 36. The expanded coils of the cover member 36 form an elongated cover that includes overlapping joints 94 (FIG. 4B) along the widthwise extent of the successive coils.

Also, as the second end 20 of the needle 16 moves past the stop plate 76, the spring portion 74 biases the stop plate 76 to its second position to cover the hole 58 directly under the needle 16 and prevent passage of the needle 16 back through the base plate 52. With the stop plate 76 in the second position, interaction of the second end 20 of the needle against the stop plate 76 prevents the hub 22 from moving back toward the base member 50, such that the needle protection assembly 14 is maintained in the extended condition with the cover member 36 surrounding the needle 16.

Although the above description refers to various components of the safety needle assembly 10 as being formed of a resin material, this description is provided for non-limiting exemplary purposes, and other materials may be used to the extent that the alternative materials provide the same functional operation of the safety needle assembly 10 described herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. In combination, a medical needle and a needle protective device, the combination comprising:
    a needle support supporting a medical needle having an exposed tip;
    a needle protection assembly including:
        a cover member having a first end attached to said needle support in surrounding relation to a portion of said medical needle, and said needle protection assembly having a retracted condition and an extended condition; and
        a base sub-assembly attached to a second end of said cover member, said base sub-assembly comprising:
    a) a base member including a planar base plate defining a through hole receiving said medical needle therethrough in said retracted condition of said needle protection assembly; and
    b) a needle stop member comprising an integrally formed spring portion and stop plate, both said spring portion and said stop plate lying on a planar side of said base plate, and said spring portion biasing said stop plate in linear movement to cover said hole in response to movement of said needle protection assembly to said extended condition.

2. The combination of claim 1, wherein said cover member comprises a spiral coil.

3. The combination of claim 2, wherein said spiral coil includes a reduced coil diameter at said first end of said cover member attached to said needle support and an enlarged coil diameter at said second end of said cover member attached to said base member.

4. The combination of claim 3, wherein said spiral coil is formed of an elongated planar member formed as a rolled planar ribbon having a width and a length, wherein the width of said planar ribbon extends generally parallel to said medical needle.

5. The combination of claim 1, wherein said integrally formed spring portion and stop plate are molded of a resin material.

6. The combination of claim 1, wherein said spring portion includes opposing arcuate sides extending from said stop plate, said arcuate sides each having a concave edge and said concave edges facing inwardly toward each other.

7. The combination of claim 6, wherein said needle stop member is movable between first and second positions, said arcuate sides being flexed outwardly from each other in said first position and biasing said stop plate in engagement against said medical needle, and said arcuate sides moving toward each other during said linear movement of said stop plate in response to movement of said needle protection assembly to said extended condition.

8. The combination of claim 6, wherein said spring portion defines a continuous inner circumference connecting said opposing arcuate sides.

9. The combination of claim 1, wherein said base plate includes first and second axially spaced planar portions generally perpendicular to said medical needle, and said second planar portion defines a recessed area in said base plate containing said needle stop member.

10. The combination of claim 9, including a stop retainer plate supported on said first planar portion of said base plate, and extending over said needle stop member to retain said needle stop member between said stop retainer plate and said second planar portion.

11. In combination, a medical needle and a needle protective device, the combination comprising:
    a needle support supporting a medical needle having an exposed tip;
    a needle protection assembly including:
        a cover member having a first end attached to said needle support in surrounding relation to a portion of said medical needle, and said needle protection assembly having a retracted condition and an extended condition; and
        a base sub-assembly attached to a second end of said cover member, said base sub-assembly comprising:
    a) a base member including a planar base plate, and an enclosure wall extending from said base plate and defining a hollow enclosure receiving said second end of said cover member, said base plate defining a through hole receiving said medical needle therethrough in said retracted condition of the needle protection assembly; and
    b) a needle stop member comprising a spring portion and stop plate, said spring portion configured as an elastically resilient ring shaped member including opposing arcuate sides extending from a proximal location attached on said stop plate to a distal location adjacent to said enclosure wall, both said spring portion and said stop plate lying on a planar side of said base plate, and said spring portion biasing said stop plate in linear movement to cover said hole in response to movement of said needle protection assembly to said extended condition.

12. The combination of claim 11, wherein said enclosure wall defines a diameter on said base plate, and a distance between said stop plate and said distal end of said spring portion is equal to about one-half said diameter.

13. The combination of claim 11, wherein said base plate includes first and second axially spaced planar portions generally perpendicular to said medical needle, and said second planar portion defines a recessed area in said base plate containing said needle stop member.

14. The combination of claim 13, wherein an axial wall extends between said first and second planar portions and defines an abutment for engaging said stop plate during said linear movement of said stop plate in response to movement of said needle protection assembly to said extended condition.

15. The combination of claim 11, wherein said needle stop member is movable between first and second positions, said arcuate sides being flexed outwardly from each other in said first position and biasing said stop plate in engagement against said medical needle, and said arcuate sides moving toward each other during said linear movement of said stop plate in response to movement of said needle protection assembly to said extended condition.

16. The combination of claim 11, wherein said cover member comprises a spiral coil formed as a rolled planar ribbon having a width and a length, wherein the width of said planar ribbon extends generally parallel to said medical needle.

17. The combination of claim 16, wherein said spiral coil includes a reduced diameter at said first end of said cover member attached to said needle support and an enlarged diameter at said second end of said cover member attached to said base member.

18. The combination of claim 11, wherein said spring portion and said stop plate are formed as an integrally molded component.

19. The combination of claim 11, wherein said needle support includes a circular flange extending perpendicular to said needle, said flange sized to rest against said enclosure wall and cover said spiral coil in said retracted condition of said needle protection assembly.

* * * * *